United States Patent
Zombo et al.

(10) Patent No.: US 7,485,882 B2
(45) Date of Patent: Feb. 3, 2009

(54) HAND HELD MAGNETIC INDUCTION THERMOGRAPHY SYSTEM

(75) Inventors: Paul J. Zombo, Cocoa, FL (US); Robert E. Shannon, Oviedo, FL (US); Max Rothenfusser, Munich (DE); Matthias Goldammer, Munich (DE); Christian Homma, Vaterstetten (DE); Joachim Baumann, Munich (DE)

(73) Assignee: Siemens Energy, Inc., Orlando, FL (US)

( * ) Notice: Subject to any disclaimer, the term of this patent is extended or adjusted under 35 U.S.C. 154(b) by 244 days.

(21) Appl. No.: 11/453,616

(22) Filed: Jun. 15, 2006

(65) Prior Publication Data

US 2008/0067455 A1    Mar. 20, 2008

(51) Int. Cl.
    *G01J 3/10* (2006.01)
(52) U.S. Cl. ............... 250/504 R; 374/4; 374/5; 374/111; 374/121; 600/549
(58) Field of Classification Search ......... 250/504 R; 374/4, 5, 111, 121; 600/549
    See application file for complete search history.

(56) References Cited

U.S. PATENT DOCUMENTS

| | | | |
|---|---|---|---|
| 4,173,970 A | 11/1979 | Momin | |
| 4,849,885 A | 7/1989 | Stillwagon et al. | |
| 4,854,724 A | 8/1989 | Adams et al. | |
| 5,124,640 A | 6/1992 | Chern | |
| 5,293,119 A | 3/1994 | Podney | |
| 5,386,117 A | 1/1995 | Piety et al. | |
| 5,562,345 A | 10/1996 | Heyman et al. | |
| 5,637,871 A | 6/1997 | Piety et al. | |
| 5,675,149 A | 10/1997 | Wood et al. | |
| 5,820,263 A * | 10/1998 | Ciobanu | 374/111 |
| 6,000,844 A | 12/1999 | Cramer et al. | |
| 6,440,084 B1 * | 8/2002 | Gentempo et al. | 600/549 |
| 6,517,236 B2 | 2/2003 | Sun et al. | |
| D473,149 S * | 4/2003 | Chiu | D10/57 |
| 6,617,847 B2 | 9/2003 | Mitra et al. | |
| 6,674,292 B2 | 1/2004 | Bray et al. | |
| 6,712,502 B2 * | 3/2004 | Zalameda et al. | 374/5 |
| 6,856,662 B2 | 2/2005 | Glass et al. | |

(Continued)

FOREIGN PATENT DOCUMENTS

EP    1 659 396 A2    5/2006

(Continued)

*Primary Examiner*—Nikita Wells
*Assistant Examiner*—Johnnie L Smith, II

(57) ABSTRACT

A hand-held thermography system (8). A generator (10) supplies current to a transformer (15) in a handle (16). An induction coil (20) connected to the transformer (15) extends from the handle (16). The induction coil (20) induces eddy currents in a test object (50), producing a thermal topography on a surface (52) of the object (50) that reveals structural features including defects in the object. An infrared camera (24) mounted on the transformer (16) digitizes images of the thermal topography. A controller (12) processes the images, displays them on a monitor (14), and stores them in a digital memory (11) for evaluation. Digitized positional data relating the position of the image to the surface may also be stored. An operator (40) presses a trigger (17), signaling the controller (12) to start current to the induction coil (20) and simultaneously to acquire and process one or more images from the camera (24). The images may be evaluated visually and/or by computerized analysis techniques for analyzing defects in the object.

14 Claims, 3 Drawing Sheets

U.S. PATENT DOCUMENTS

| | | |
|---|---|---|
| 6,991,368 B2 * | 1/2006 | Gerlitz .................. 374/121 |
| 7,115,098 B2 * | 10/2006 | Gentempo et al. ......... 600/549 |
| 2002/0050566 A1 | 5/2002 | Nilsson et al. |
| 2002/0151817 A1 * | 10/2002 | Gentempo et al. ......... 600/549 |
| 2005/0270037 A1 | 12/2005 | Haynes et al. |
| 2007/0230536 A1 * | 10/2007 | Zenzinger et al. ............ 374/4 |

FOREIGN PATENT DOCUMENTS

| | | |
|---|---|---|
| JP | 08201323 A | 8/1996 |

* cited by examiner

A # HAND HELD MAGNETIC INDUCTION THERMOGRAPHY SYSTEM

FIELD OF THE INVENTION

The invention relates to the field of non-destructive evaluation of articles of manufacture by stimulating an article with electromagnetic energy, then imaging and evaluating a resulting topography of differential inductive heating on a surface of the article.

BACKGROUND OF THE INVENTION

Active thermography is a non-destructive evaluation (NDE) technique in which a non-destructive stimulation such as acoustic or electromagnetic energy is applied to a test object. The applied energy induces mechanical vibrations or electromagnetic currents (respectively) in the object, thereby producing an uneven temperature distribution in the object. Structural features and flaws in the object generate localized heat under such stimulation. A resulting temperature topography on a surface of the object is imaged with an infrared camera. Information about defects and the inner structure of the object can be obtained by evaluating the images individually or a time series of such images. Each image may be digitized into picture elements, or pixels, with each pixel representing a small unit area on the surface. These digitized images can then be used for digital displays and for computer analyses, in which a temperature/time series of images may be processed and analyzed by pixel over time and in patterns of pixels over time and/or space. Time series information improves overall sensitivity of the technique, and facilitates the determination of geometric quantities like local coating thickness, wall thickness, or depth of a defect.

Stationary inspection systems are generally used to test articles of manufacture during their production. Mobile systems are often used for field inspections of operational apparatus such as aircraft, power plant equipment, transportation equipment, and the like. Current NDE techniques such as dye penetrant, magnetic particle coatings, ultrasonic stimulation, and eddy current stimulation have various disadvantages in speed, flexibility and/or potential contamination to the articles tested. Improved NDE devices and techniques are needed.

BRIEF DESCRIPTION OF THE DRAWINGS

The invention is explained in following description in view of the drawings that show.

DETAILED DESCRIPTION OF THE INVENTION

Figure 1:
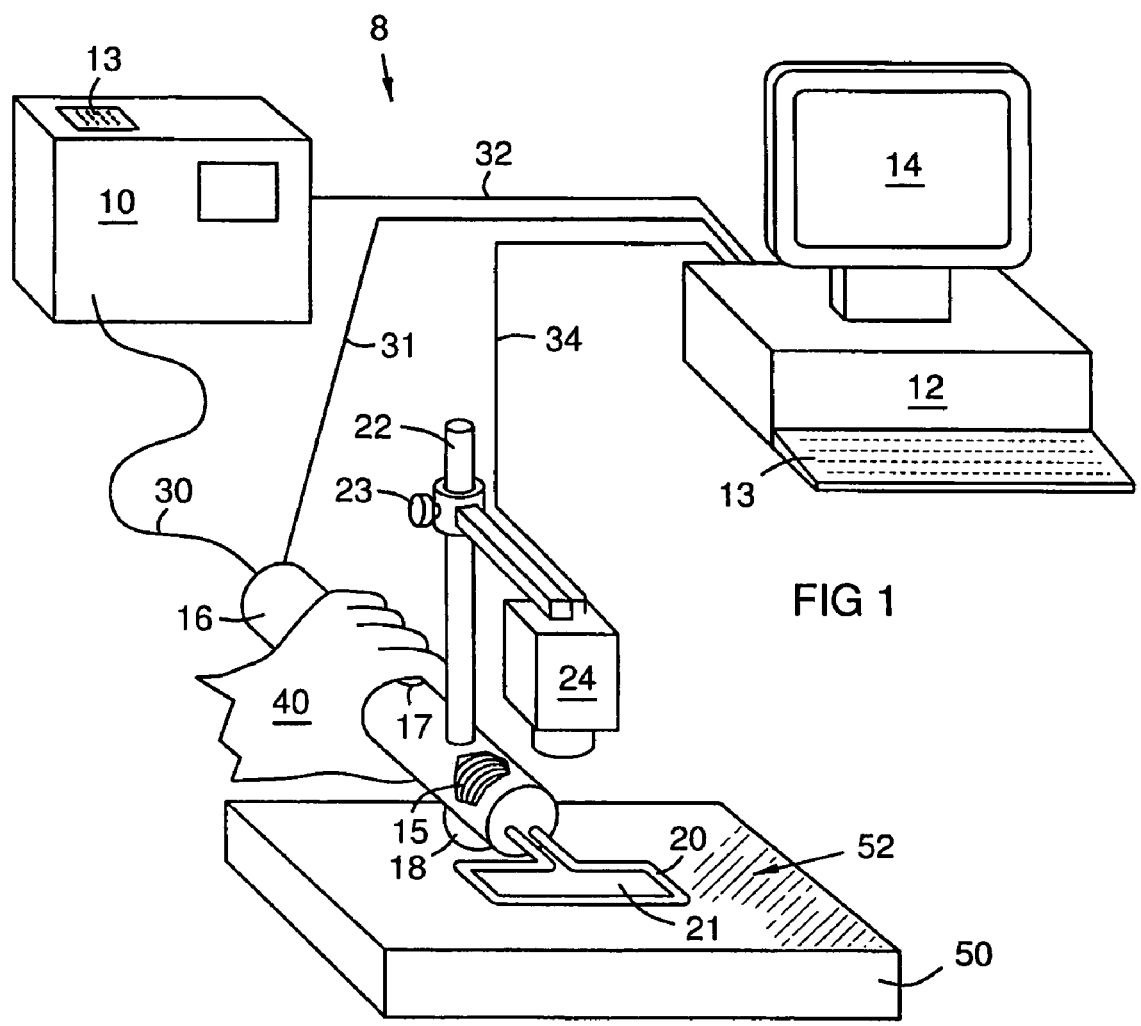
FIG. 1 schematically illustrates a hand-held thermography system in accordance with the invention.

FIG. 1 illustrates a thermography system 8 with an electric current generator 10 electrically connected 32 to a processor or controller 12 with a display 14. The connection 32 provides control and status signals between the controller and the generator 10. The generator 10 provides pulsed alternating current (10 ms-1,000 ms bursts) to a transformer 15 in a handle 16 via an electrical cord 30. A digital infrared camera 24 may be mounted on the handle 16 on a support 22 and may be electrically connected 34 to the controller 12. The camera support 22 may have a camera position adjustment mechanism 23. An induction coil 20 extends from the transformer 15, and may have a generally planar frame shape. The induced current is highest directly underneath the coil winding and decreases with increasing lateral distance from the winding. Therefore, an inner and outer border area with a width defined by the distance from the winding where the current decays to a certain extent (for example by 50%) can be used for thermographic inspection. The effective test area is a function of many variables, such as the amount of current in the coil 20, the properties of the test object 50, and the sensitivity of the camera 24. The test area surrounding the coil 20 is transparent to infrared radiation emitted from the test object 50. The entire inner zone of the coil 20 may be used for test purposes if the induced currents are sufficiently high. A trigger 17 connected 31 to the controller 12 may be provided on the handle 16 to start current flow in the induction coil 30. The trigger 17 connected 31 to the controller 12 may also be used to start the imaging sequence from camera 24. A second handle (not shown) may be provided for two-handed operation. If so, for additional safety a trigger 17 may be provided on both handles, and the controller 12 may require both triggers to be pressed to energize the induction coil 30.

The transformer 15 transforms electrical current provided by the generator 10 into current suitable for the induction coil 20. The transformer may be a step-down type with a voltage ratio such as 10:1 and a corresponding amperage ratio such as 1:10. For example, the generator 10 may provide an alternating current of about 100-1,000 volts, 10-100 amps, and frequency of about 10 to 1000 kHz. The transformer 15 may convert the current to about 10-100 volts, and 100-1,000 amps for the induction coil 20. A coaxial transformer design is especially suitable for hand-held operation due to its size and weight.

Placing a transformer 15 in the handle 16 reduces current in the cable 30 that would otherwise be needed between the generator 10 and the handle 16. This reduces resistive heating in the cable 30, which avoids damage to the cable 30. The current and transformer parameters above are provided as examples only. The generator 10 may provide current with user-selectable characteristics to the induction coil 20, as selected from a user input device 13 on the generator 10 or the controller 12 or the transformer 15, as known in electronics. For example, the user input device 13 may be a keyboard, keypad, or dial interfaced to the controller 12. Electric current parameters for the induction coil 20 may be selected based on the application or type of test object. For test objects with a high electric conductivity (copper, aluminum, etc.), the resistive heating and thus the temperature rise is low. In this case, the amplitude of the excitation current must be chosen to be sufficiently high to obtain meaningful results. The excitation frequency determines the "skin depth", a parameter that describes the penetration depth of the induced current. Resistive heating occurs only in the skin depth layer immediately adjacent to the surface, and may vary from only a few micrometers for magnetic materials to some meters for materials with low electrical conductivity, such as carbon composite materials.

Figure 4:
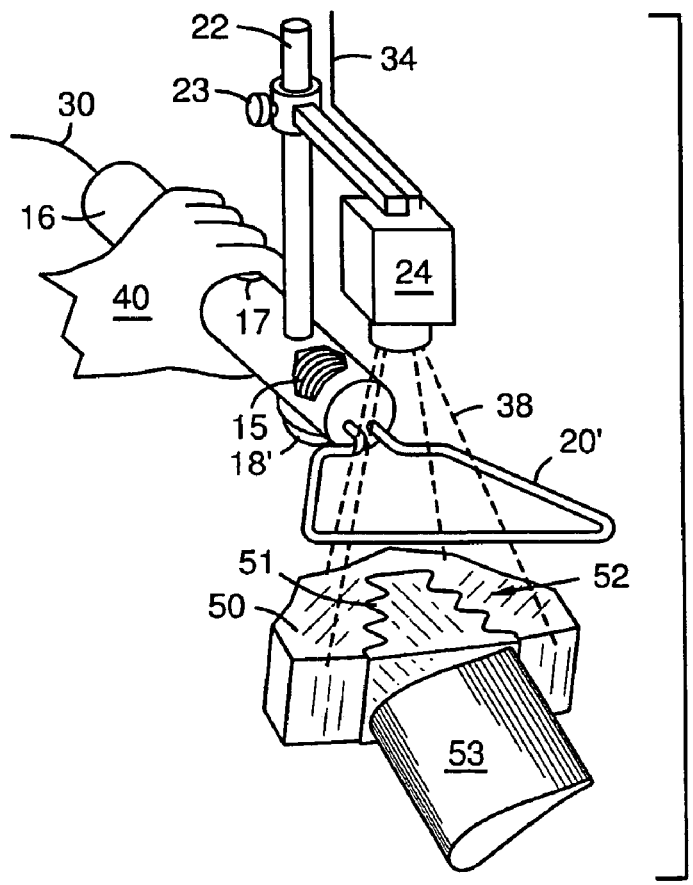
FIG. 4 illustrates an offset induction coil shape and a spacer/digitizer.
Figure 5:
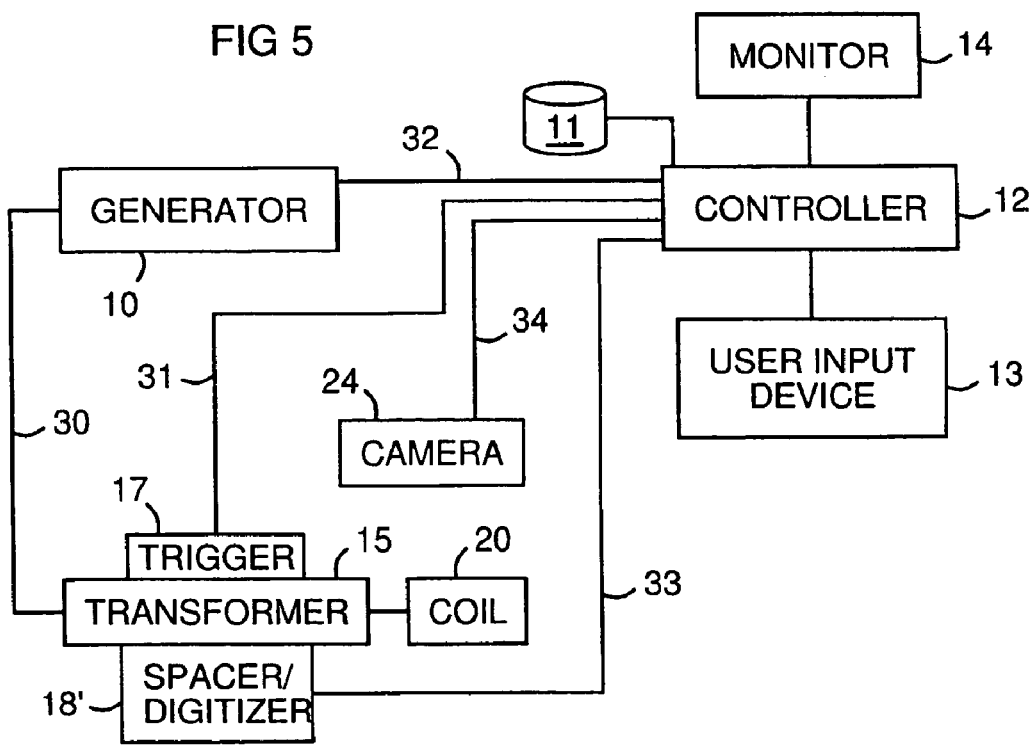
FIG. 5 is a schematic diagram of components.

FIG. 1 shows a generally rectangular induction coil 20 with the camera 24 pointing to an area 21 surrounded by the induction coil 20. However, other coil shapes may also be used, such as rectangular, circular, etc. For curved test objects a bending of the coil may be appropriate. Coils with only one winding may be used; however, multiple windings may be appropriate in some applications. The inductance of the coil 20 should match the output properties of the excitation device. FIG. 4 shows an induction coil 20' formed with a shape corresponding to the cross-sectional shape of a blade root 51 of a turbine blade 53, with the camera field of view 38 including the critical blade root region. The orientation of the induction coil 20' is particularly useful in this embodiment because it contains sections oriented approximately perpendicular to the orientation of cracks that may be expected to develop in this region of the turbine. The perpendicular orientation provides a maximum sensitivity for the detection of such flaws. The embodiment of FIG. 4 is operated by moving the induction coil 20' along a surface 52 of the turbine disk 50, or holding the coil 20' still while the turbine disk 50 is rotated, while taking a series of images. The images may be triggered manually by the operator pressing a trigger 17 or automatically by the controller 12, based on a time or space interval. The induction coil 20' is thermally insulated to reduce its impact on the thermographic images.

Figure 2:
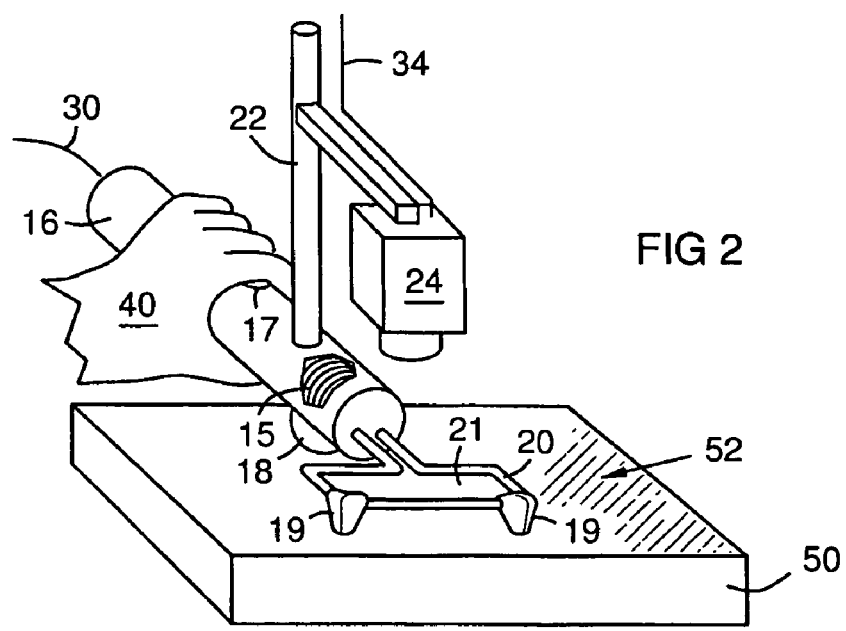
FIG. 2 illustrates additional induction coil spacers for 3-point spacing.

To provide consistent spacing between the induction coil 20 and the test surface 52, at least one spacer 18 may be attached to a side of the handle 16 to provide contact with the surface 52. As shown in FIG. 2, additional spacers 19 may be provided on the induction coil 20 or on the handle 16 to separate the test surface 52 from the induction coil 20 along a line or plane of contact with the test surface 52 that is generally parallel to the induction coil 20. Two points of contact can be used to establish a line of contact, or three points of contact may be used to establish a plane of contact. For stationary testing, the spacer 18 may be stationary. In this case, the operator 40 may hold the induction coil 20 in one position on the surface 52 after starting the stimulation, while the controller 12 processes one or more images. For moving testing, the spacer 18 may be in the form of a low friction skid or a rotating ball or wheel. FIG. 4 shows the spacer 18' as a position detector such as a digitizer ball used on a computer mouse, that is electronically connected 30 to the controller 12 to track the motion of the induction coil 20' over the surface 52. The controller 12 may use this input to operate the camera 24 to acquire images with a known spatial relationship. With digitizer input the controller 12 may also dynamically adjust the current in the induction coil 20' in proportion to the speed of induction coil motion. Alternately, the controller 12 may start the induction coil current upon triggering, then input a time series of images, and then display a message prompting the operator to move the induction coil 20'. The controller 12 may be a programmable logic controller, or it may be a circuit card interfaced to a computer, for example. The controller 12 may include a clock circuit and/or may use a clock signal provided by a computer to calculate time intervals and speeds of digitizer 18' motion.

Figure 3:
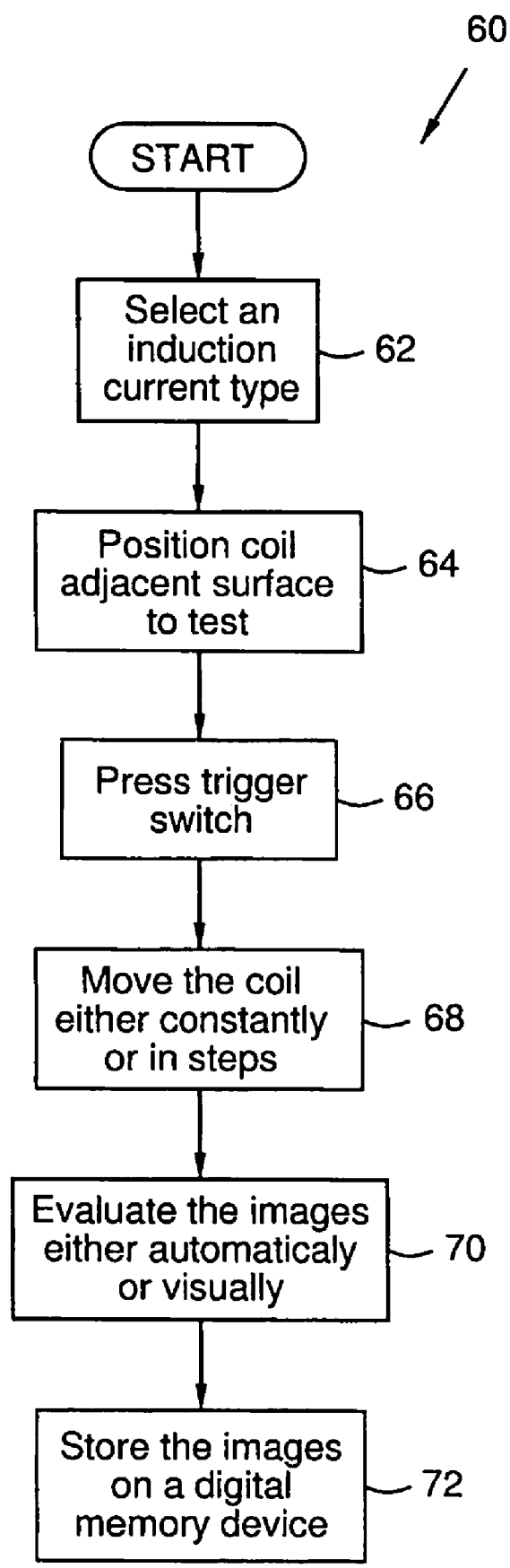
FIG. 3 illustrates a method of operation of the invention.

Referring now to FIG. 3, to operate 60 the system 8 to inspect an article of manufacture 50, a user selects 62 electrical parameters via the input device 13, then holds 64 the induction coil 20 adjacent to a surface 52 on an article 50 to be tested, and presses 66 the trigger 17. In one embodiment, triggering causes the controller to start current pulse in the induction coil 20, and contemporaneously (i.e. simultaneously or immediately thereafter) to input one or more images from the camera 24. In this embodiment, the user then moves 68 the induction coil 20 to another position and repeats. On an embodiment with a digitizer 18', pressing the trigger may cause the controller 12 to initiate repeated current bursts (repetition rate typically 0.5-50 hertz), automatic image acquisition, and positional input by the digitizer 18'. In a digitizer embodiment, the user may move 68 the induction coil over the test surface 52 continuously, while the controller 12 controls image acquisition and digitizer position input.

The images may then be evaluated 70 visually by display on the monitor 14 and/or by computerized image analysis techniques. The images may be stored 72 on a digital memory device 11 such as a disc drive.

The images acquired for each current pulse may optionally be post-processed, such as by background subtraction or pulse-phase analysis. Background subtraction is a technique used in thermography wherein the first image of the recorded infrared sequence corresponds to the initial status of the test sample before heating and is subtracted from the following images. This eliminates a potential non-uniform infrared emissivity of the sample surface due to inhomogeneous material properties, dirt, etc. Pulse-phase analysis is used to evaluate not only the amplitude but also the time behavior of the temperature signal. A sinusoidal signal (e.g. with a period in the order of two pulse lengths) is correlated with the measured time signal. The calculated phase of the sinusoidal signal corresponds to the time delay of the induced heat flow and the amplitude to the temperature rise. From the time delay, the depth of a defect can be evaluated. Both techniques provide lateral resolved information because they are applied to each pixel of a series of images.

In tests of a prototype, detection of discontinuities in a test object 50 was more sensitive when the induction coil 20 was closer to the test surface 52. Distances up to about 20 mm provided sufficient sensitivity to detect fatigue cracks in metal superalloy parts. The hand-held design allows an operator to make continuous adjustments in the angle of the induction coil 20 in order to test parts with various curvatures and shapes. The induction coil 20 may be optimally sized for a particular application. For example, to inspect a turbine disc the induction coil 20 may be made about the size of a blade attachment slot.

The induction coil 20 may be actively cooled, although active cooling may not be required when operating with pulsed current. For active cooling, the winding of the induction coil may be hollow and attached to a water circulation system with a heat exchanger. The coil winding may be insulated to minimize heat emission that would produce "noise" on the camera image, and could thus mask defect indications.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

The invention claimed is:

1. A hand-held thermography system comprising:
   an electric current generator;
   a handle;
   a transformer in the handle, the transformer electrically connected to the electric current generator;
   an induction coil electrically connected to the transformer, and extending from the handle;
   a digital infrared camera attached to the handle by a camera support that holds the digital infrared camera facing an area adjacent to the induction coil; and
   a processor connected to the digital infrared camera for receiving, storing, and displaying infrared images digitized by the infrared camera.

2. A hand-held thermography system as in claim 1, further comprising a spacer attached to the handle for positioning the induction coil at a predetermined distance of separation from a surface of an object to be tested.

3. A hand-held thermography system as in claim 1 wherein the electromagnetic induction coil is formed as a generally planar frame around an inner area that is transparent to infrared energy, and the digital infrared camera is held facing said inner area by the camera support.

4. A hand-held thermography system as in claim 1, wherein the induction coil is formed to correspond to a cross-sectional shape of a turbine blade root.

5. A hand-held thermography system as in claim 1, further comprising a trigger on the handle, the trigger electrically connected to the processor, the processor responding to a signal from the trigger by controlling an electrical current from the generator to the induction coil and by contemporaneously inputting at least one image from the infrared camera.

6. A hand-held thermography system as in claim 5, wherein the electric current generator provides user selectable parameters of electric current to the induction coil via a user input device interfaced to the electric current generator or the processor.

7. A hand-held thermography system as in claim 1, further comprising a position detector attached to the handle for inputting positional data to the processor representing positions of the images relative to a surface being inspected.

8. A hand-held thermography system comprising:
   an electric current generator;
   a handle;
   a transformer in the handle, the transformer electrically connected to the electric current generator;
   an induction coil electrically connected to the transformer, and extending from the handle;
   a spacer associated with the handle for positioning the induction coil at approximately a predetermined distance of separation from a surface of an object to be tested;
   a digital infrared camera attached to the handle by a camera support that holds a field of view of the digital infrared camera facing an area adjacent to the induction coil;
   an electronic controller and a monitor electrically connected to the digital infrared camera for receiving, storing, and displaying infrared images digitized by the infrared camera; and
   a trigger on the handle, the trigger electrically connected to the controller, the controller responding to a signal from the trigger by controlling an electrical current from the generator to the induction coil and contemporaneously inputting at least one image from the infrared camera.

9. A hand-held thermography system as in claim 8, wherein the spacer comprises one of the group consisting of a low friction skid, a rotating ball, and a wheel.

10. A hand-held thermography system as in claim 8, further comprising a position detector attached to the handle for inputting positional data to the controller representing positions of the images relative to a surface being inspected.

11. A hand-held thermography system as in claim 8, wherein the induction coil is formed to correspond to a cross-sectional shape of a turbine blade root.

12. A hand-held thermography system as in claim 11, wherein the induction coil is thermally insulated.

13. A method for using the hand-held thermography system of claim 6 to inspect an article of manufacture, the method comprising:
   a) selecting induction current parameters;
   b) placing the induction coil adjacent to a first area on a surface of the article of manufacture;
   c) pressing the trigger to activate the electric current to the induction coil and to input at least one image from the digital infrared camera to the controller;
   d) moving the induction coil to another area of the surface; and
   e) repeating steps b) and c) and d) until a desired portion of the surface has been thermographically imaged.

14. A method as in claim 13, further comprising inputting positional data to the controller representing relative positions of the images on the surface.

* * * * *